United States Patent [19]

Shanzer et al.

[11] Patent Number: 4,631,291
[45] Date of Patent: Dec. 23, 1986

[54] ENTEROBACTIN TYPE COMPOUNDS

[75] Inventors: Abraham Shanzer, Rishon-Le-Zion; Jacqueline Libman, Rehovot, both of Israel

[73] Assignee: Yeda Research & Development Co. Limited, Rehovot, Israel

[21] Appl. No.: 617,465

[22] Filed: Jun. 5, 1984

[30] Foreign Application Priority Data

Jun. 8, 1983 [IL] Israel ........................................ 68929

[51] Int. Cl.[4] ................. C07D 323/00; C07D 405/12; A61K 31/365
[52] U.S. Cl. .................... 514/450; 514/336; 514/312; 514/314; 514/333; 514/397; 549/267; 546/268; 546/156; 546/168; 546/256
[58] Field of Search ............... 546/256, 268, 168, 156; 549/267; 548/336; 424/263, 279, 258, 273 R; 514/450, 336, 312, 314, 333, 397

[56] References Cited
PUBLICATIONS

Rastetter et al., J. Org. Chem. 1980, 45(24) 5011–12; 1981, 46(18), 3579–3590.
Rogers CA. 93 188622b.
Pecoraro et al. CA. 99:32146n.
Corey et al., Tetrahedron Letters 45, 1977, 3919–3922.

Primary Examiner—Jane T. Fan
Attorney, Agent, or Firm—Browdy and Neimark

[57] ABSTRACT

There are provided novel enterobactin type compounds. There is provided a novel process for the production of enterobactin, and of novel enterobactin type compounds which process is based on the reaction of a serine derivative with a stannoxane of the [BU$_2$Sn-(OCH$_2$CH$_2$O)] type. Enterobactin is a known compound of known utility. The novel derivatives are valuable as sequestering agents for iron and other transition metals, for the separation and analysis of same. They can be used as active ingredients in pharmaceutical compositions for the removal of such metals accumulated above an acceptable level in patients.

2 Claims, 1 Drawing Figure

U.S. Patent    Dec. 23, 1986    4,631,291
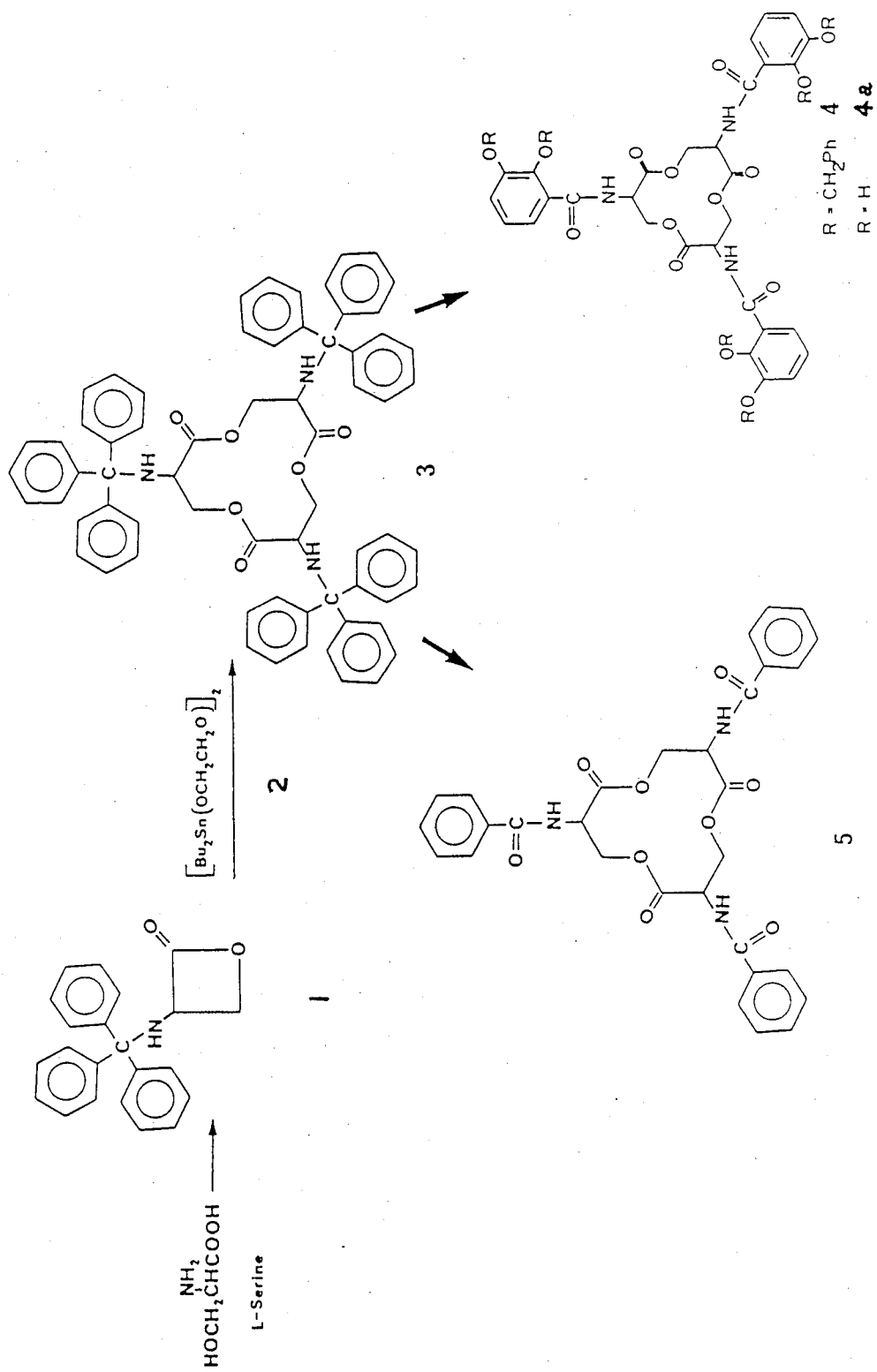

ENTEROBACTIN TYPE COMPOUNDS

FIELD OF THE INVENTION

The invention relates to the synthesis of certain enterobactin type compounds by a novel method and to certain novel derivatives of enterobactin thus obtained. The invention further relates to certain processes and compositions based on the novel derivatives.

BACKGROUND OF THE INVENTION

The compound enterobactin is a very effective sequestering agent for iron, forming an unusual macro-bridged hexacoordinate trianon. Enterobactin is capable of removing iron even from Transferrin. It is produced in small quantities by E. Coli and related enteric bacteria when grown on iron deficient media. Chemically, enterobactin comprises three serine molecules linked to a macrocyclic trilactone substituted by three catechol residues as ligating side chains. This compound has been prepared by total synthesis by Corey et Bhattacharyya, Tetr. Letters 3919 (1977). Another synthesis of enterobactin has been reported by Rastetter, J. Org. Chem 45, 5012 (1980). Both methods of synthesis are based on the stepwise condensation of serine derivatives to a linear trimer and the subsequent cyclization of same.

SUMMARY OF THE INVENTION

The invention relates to a novel method for the synthesis of enterobactin and of related compounds. The derivatives of enterobactin thus obtained are novel per se and thus form part of the invention. The products obtained according to the process of the invention are enterobactin, which is a known compound of known utility, and derivatives of this compound.

The novel process has many advantages in the production of this compound. The novel compounds are valuable sequestering agents for metals such as iron and transition metals. They can be used in analysis and for separation of such metals. The novel compounds are valuable as active ingredients of pharamaceutical compositions for the removal of excess of metals, such as iron, accumulated in patients suffering from certain maladies and disorders, such as Cooley's anemia. The compounds can also be used as tools in diagnostic imaging devices for the fast removal of radioactive tracers such as radioactive gallium.

The novel compounds can also be used in drug delivery systems for the delivery of required metal cations.

The novel method is based on the use of cyclic tin-oxygen compounds as templates which affect the self condensation on $\beta$-lactones to macrocyclic polylactones. The synthesis comprises cyclization of $\beta$-lactone derived from tritylated serine to the enterobactin skeleton in a single condensation step, and subsequent replacement of the trityl (or other protective group) by a suitable group —CO—R, where R designates alkyl, fluoroalkyl, aryl, pyridyl, hydroxyquinolyl, bipyridyl, imidazolyl, 2,3-dihydroxyphenyl, 2,3-bis(benzyloxy)phenyl, to provide the desired derivatives.

BRIEF DESCRIPTION OF THE DRAWING

The FIGURE shows a chemical reaction formula of a process in accordance with the present invention.

DETAILED DESCRIPTION OF PREFERRED EMBODIMENTS

In the process of the present invention, use of the $\beta$-lactone derived from tritylated serine is essential for obtaining the enterobactin skeleton. Other serine derivatives such as the N-carbobenzoxy serine of N-2,3-bis(benzyloxy)benzoyl serine failed to provide the corresponding $\beta$-lactones. Moreover the cyclization reactions of $\beta$-lactones is limited to a few derivatives; for instance, 4,4-dimethyloxetanone, 4-methyloxetanone, 3,3-dimethyloxetanone and 3-methyloxetanone failed to provide macrocyclic products when reacted with the stannoxane.

By starting with the optically active $\beta$-lactone of tritylated L-serine, there is obtained the L,L,L-tritylated compound of formula 3 shown in the drawing and from this the L,L,L-derivatives such as those shown in formulae 4 and 5 of the drawing.

Although the invention is illustrated with reference to tritylated serine starting compounds, resulting in a tritylated enterobactin type ring system, it ought to be clearly understood that instead of the trityl group there may be used another suitable protective group, such as carbobenzoxy, trifluoroacetyl, dibenzyl.

The substituent R may designate a group selected from lower alkyl, phenyl, pyridyl, bipridyl.

According to a preferred embodiment of the invention the tritylated enterobactin system compound is reacted to remove the trityl (or other protective group) and this is accomplished by heating with a mineral acid such as hydrogen chloride in ethanol, or with acetic acid, or by treatment with trifluoracetic acid, or by hydrogenation in the presence of a mineral acid, resulting in the corresponding ammonium salt, which is acylated so as to give the desired product. Suitable acylating agents are compounds such as nitrophenolate of 2,3-bis(benzyloxy)benzoic acid, of picolinic acid, of hydroxyquinolylcarboxylic acid, of bipyridylcarboxylic acid, of imidazolylcarboxylic acid, or an aliphatic, fluoroaliphatic, or aromatic acyl halide, resulting in the formation of compounds of the formula

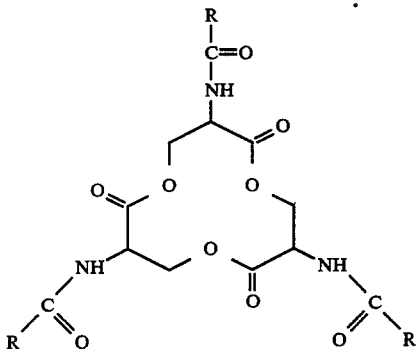

wherein R is 2,3-bis(benzyloxy)phenyl, pyridyl, hydroxyquinolyl, bipyridyl, imidazolyl, alkyl, fluoralkyl, aryl respectively. The benzylated derivatives are subsequently subjected to hydrogenolysis to yield the desired final product.

Compounds which can thus be prepared are enterobactin or the tris(alkylcarboxamide), tris(fluoroalkycarboxamide), tris(arylcarboxamide), tris(pyridylcarboxamide), tris(hydroxyquinolylcarboxamide), tris(- bipyridylcarboxamide, and tris(imidazolylcarboxamide) analogs of same.

When the starting compound is L-serine, there is obtained the L,L,L-enterobactin isomer, and in a corresponding manner the corresponding L,L,L-isomers of same wherein R is as defined above.

When the starting compound is D,L-serine, there is obtained the racemic enterobactin compound and also the corresponding racemic derivatives of same with R as defined above.

This applies to the process starting with the D-derivative of serine, which results in the optically active D-isomers.

Amongst uses of the compounds defined above there may be mentioned: components of membranes for the analysis and separation of specific salts, sequestering agents for the removal of metal overdoses, and drug delivery systems for the administration of needed metal cations.

The present invention will now be illustrated by means of the following examples. The reference numerals in the following examples refer to the formulae shown in the attached drawing.

EXAMPLE 1

Preparation of L-N-trityl-oxetanone 1

5.52 g (0.016 mol) L-N-tritylserine are dissolved in 400 ml dry methylene chloride and treated at 0° C. with 390 mg (0.0032 mol) dimethylaminopyridine and 2.4 ml (0.016 mol) diisopropylcarbodiimide. The reaction mixture is then stirred at room temperature for 2 days, concentrated in vacuo and chromatographed on silicagel Merck 60. Elution with benzene or toluene provides 1.365 g (0.0042 mol, 26%)-lactone 1.

EXAMPLE 2

Preparation of Trilactone 3

Oxetanone 1 (1.0 g, 0.003 mol) is treated with 290 mg (0.0005 mol) stannoxane 2 in 25 ml dry chloroform for 2½ hrs under reflux. Concentration in vacuo and chromatography of the crude reaction mixture on silicagel, Merck 60, (elution with toluene-ethyl acetate, 7:3) gives 230 mg (23%) of trilactone 3. Trilactone 3 exhibits mp 110°–112° C., I.R. (CHCl$_3$)μ, 1736, 1585, and 1216 cm$^{-1}$; nmr (CDCl$_3$), δ7.48 (m 6H), 7.22 (m 9H), 3.85 and 3.67 (m, 1H), 3.36 (m, 2H) and 2.66 ppm (m 1H), $[\alpha]_D D = +53.0°$ (CHCl$_3$, c=0.6).

EXAMPLE 3

Preparation of Hexabenzyleneterobactin 4

Trilactone 3 (262 mg, 2.6.10$^{-4}$ mol) are heated with 0.9 ml of 0.858N HCl in ethanol at 100° C., until the ammonium salt precipitates (ca 2-min). Then the mixture is concentrated in vacuo, the residue washed with ether and then dissolved in 2 ml dry DMF. The ammonium salt solution is then cooled in an ice bath and treated successively with 0.12 ml triethylamine and a solution of 405 mg (8.9.10$^{-4}$ mol) nitrophenolate of 2,3-bis(benzyloxy)benzoic acid in 2 ml DMF. The reaction mixture is stirred overnight at room temperature, then concentrated in vacuo and the residue extracted with ethylacetate to give 322 mg of crude material. Chromatography on Silicagel Woelm (60–100) and elution with chloroform-ethanol, 95.5, provides 50 mg trilactone 4.

EXAMPLE 4

Preparation of Enterobactin 4a 50 mg hexabenzylated enterobactin 4a are dissolved in 20 ml dry ethanol and hydrogenated at room temperature and atmospheric pressure in the presence of 50 mg Pd/C, 5%. Filtration of the reaction mixture and concentration in vacuo provides enterobactin 4a, which proved to be identical with an authentic sample.

EXAMPLE 5

Preparation of the Tribenzamide Analog 5 of Enterobactin 350 mg of trilactone 3 (3.710$^{-4}$ mol) were heated for 2 min at 100° C. with 1.3 ml of a 0.858N HCl in ethanol. Then the mixture was concentrated in vacuo, washed with ether, and the residue dissolved in 20 ml dry methanol. After cooling in an ice bath 0.306 ml triethylamine and subsequently 0.127 ml benzoylchloride were added and the mixture allowed to stir for 1 hr at room temperature. Concentration in vacuo and chromatography on silicagel (Merck) gave (after elution with chloroform-methanol=95-5) 63 mg of the benzamide 5, m.p. 90° C.

Starting with trilactone 3, and reacting with a nitrophenolate or other activated ester or acylhalide of picolinic acid, of hydroxyquinolylcarboxylic acid, of bipyridylcarboxylic acid, of imidazolylcarboxylic acid, of acetic acid or trifluoroacetic acid, the tris(pyridylcarboxamide), tris(hydroxyquinolylcarboxamide), tris(-bipyridylcarboxamide), tris(imidazolylcarboxamide), triacetamide or trifluoroacetamide were obtained respectively. In a similar matter the various derivatives defined with reference to the general formula can be prepared.

We claim:

1. An enterobactin-type compound of the formula

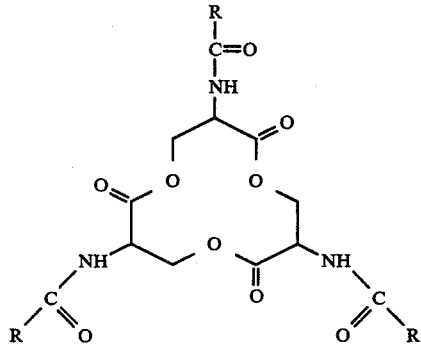

wherein R designates lower alkyl, fluoro-lower-alkyl, phenyl, pyridyl, hydroxyquinolyl, bipyridyl or imidazolyl.

2. A pharmaceutical composition for the removal of unwanted excess of metal cations accumulated in the human body, comprising a pharmaceutical carrier, and, as active ingredient, an effective amount of an enterobactin-type compound in accordance with claim 1.

* * * * *